United States Patent [19]

Osborne

[11] 4,441,358
[45] Apr. 10, 1984

[54] AUTOMATED ULTRASONIC SOLUTION VISCOMETER

[76] Inventor: Robert L. Osborne, 302 Chatham St., Avondale, Pa. 19311

[21] Appl. No.: 328,376

[22] Filed: Dec. 7, 1981

[51] Int. Cl.³ .............................................. G01N 11/06
[52] U.S. Cl. ................................................................ 73/55
[58] Field of Search ...................... 73/55, 599, 861.18, 73/861.23, 747

[56] References Cited

U.S. PATENT DOCUMENTS

| | | | |
|---|---|---|---|
| 2,048,305 | 7/1936 | Ubbelohde | 73/55 |
| 2,966,056 | 12/1960 | Heller | 73/61 R |
| 3,071,961 | 1/1963 | Heigl et al. | 73/55 |
| 3,105,379 | 10/1963 | Ellison et al. | 73/55 |
| 3,194,057 | 7/1965 | Richard | 73/599 X |
| 3,553,636 | 1/1971 | Baird | 73/599 X |
| 3,699,804 | 10/1972 | Gassmann et al. | 73/55 |
| 3,713,328 | 1/1973 | Aritomi | 73/55 |
| 3,798,960 | 3/1974 | Glass | 73/55 |
| 3,886,794 | 6/1975 | McShane | 73/861.23 |
| 4,118,973 | 10/1978 | Tucker et al. | 73/55 |
| 4,182,177 | 1/1980 | Prough | 73/290 V |
| 4,248,085 | 2/1981 | Coulthard | 73/861.23 X |
| 4,327,587 | 5/1982 | Docekal et al. | 73/599 X |
| 4,361,041 | 11/1982 | Piper | 73/599 X |

FOREIGN PATENT DOCUMENTS 570781 9/1973 U.S.S.R. ............................ 73/290 V

Primary Examiner—Gerald Goldberg
Assistant Examiner—Joseph W. Roskos
Attorney, Agent, or Firm—Mortenson & Uebler

[57] ABSTRACT

Apparatus and method are provided to automatically measure the viscosity of a solution. The apparatus employs at least two sets of piezo electric ultrasonic accoustical transducers mounted along the length of a modified viscosity tube. As the meniscus of the liquid being measured passes the first transducer, a timer is actuated. As the meniscus passes the second transducer, the timer is stopped. The measured time interval enables calculation of the solution viscosity. This invention provides highly improved accuracy and decreased test time for solution viscosity measurements, while eliminating the variables encountered in conventional optical or thermistor measurements resulting from the opacity or thermal conductivity of the liquid being measured.

5 Claims, 5 Drawing Figures

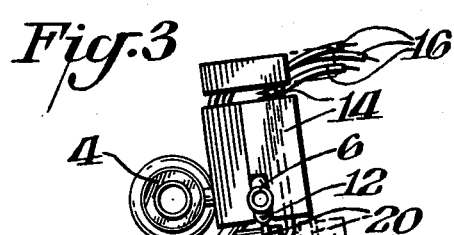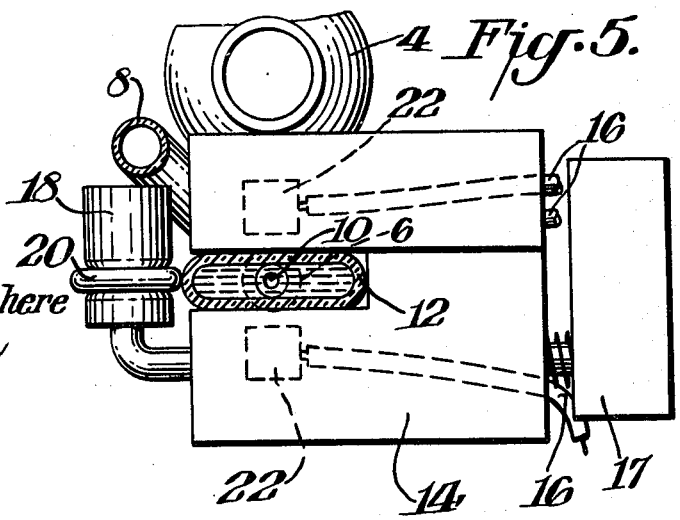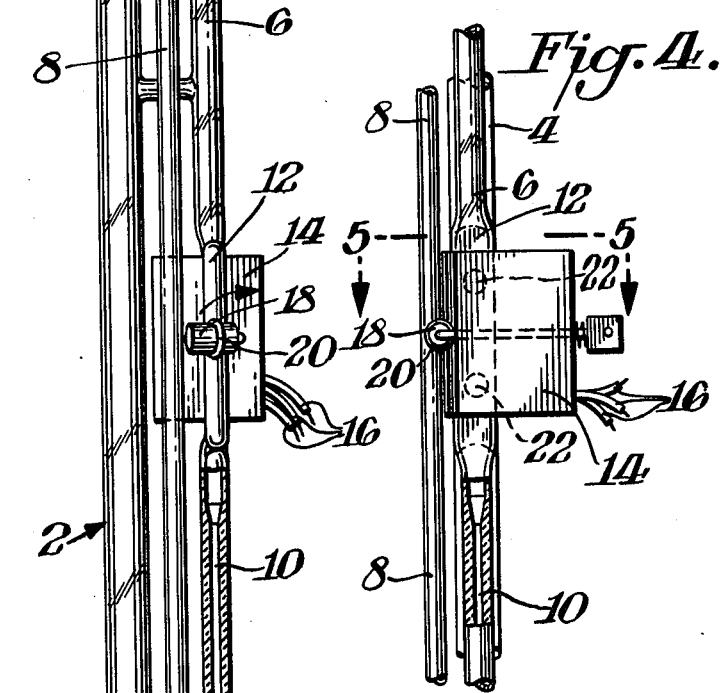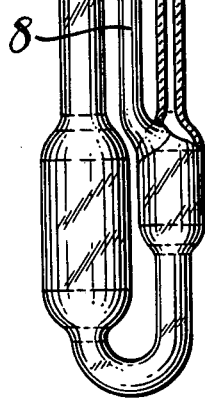

AUTOMATED ULTRASONIC SOLUTION VISCOMETER

BACKGROUND OF THE INVENTION

1. Field of the Invention

This invention relates to a method and apparatus for automatically measuring the viscosity of a solution or other liquid.

2. Description of the Prior Art

Many methods and apparatus for measuring viscosities of liquids are known and described in the prior art. One method of measuring the viscosity of a liquid is to cause it to flow along a fine transparent tube, usually a capillary tube, and to note the time taken for the liquid to pass between two spaced points on the tube. The viscosity can be determined from the time interval so obtained by comparing the time of flow with the time taken by a standard fluid, such as water or aniline, having a viscosity that is already known in identical conditions of temperature, pressure and so forth. This is a tedious procedure and liable to error.

Automatic viscosity measuring devices such as disclosed in U.S. Pat. No. 3,071,961 are known to the art. In this reference, paired light beam photodetectors are used to detect the downward flow of oil under controlled conditions from which the viscosity can be computed.

U.S. Pat. No. 3,713,328 discloses apparatus for automatically measuring the viscosity of a liquid comprising a Lantz-Zeitfuchs type reverse flow viscometer, a timing means actuated by photoelectric devices consisting of pairs of photoelectric cell and light source, and a sequence control system. The viscometer is placed in a constant temperature bath and has a timing bulb encasing light source lamps and photoelectric cells in pairs at the upper and lower timing marks of the bulb.

Various other types of sensors are known for measuring viscosities of liquids by detecting the time interval of passage of the liquid between two points in a capillary tube. The use of spark detectors to detect a meniscus of a flowing oil is known and can be used in place of photodetectors. A number of disadvantages are associated with the use of either photocell detectors or spark detectors. Photocell detectors are not satisfactory for use in measuring black oils and they require an inordinate amount of space and wiring to make them operational. On the other hand a spark detector system requires a high voltage circuit that may cause difficulties with other circuits in the instrument. In addition, the spark system generates excessive electronic noise, particularly in the low voltage control circuits and in the many computer circuits and there is a potential explosion hazard when high-voltage sparks are used. Water in the oil can interfere with spark detectors.

U.S. Pat. No. 3,798,960 discloses the use of thermistors mounted in a capillary wall and extending into the flowing stream to detect the passage of a meniscus.

U.S. Pat. No. 3,939,406 discloses use of microwaves to detect pressure drop and velocity of fluid flow. Therein, a microwave fluid flow meter is described utilizing two spaced microwave sensors positioned along a fluid flow path. Each sensor includes a microwave cavity having a frequency of resonance dependent upon the static pressure of the fluid at the sensor locations. The resonant response of each cavity with respect to a variation in pressure of the monitored fluid is represented by a corresponding electrical output which can be calibrated into a direct pressure reading. The pressure drop between sensor locations is then correlated as a measure of fluid velocity.

A radiation source has been known to be useful in detecting meniscus positions in capillary tube type automatic viscometers. U.S. Pat. No. 3,908,441 discloses a liquid level detection device which includes a transparent tube for containing a liquid which forms a meniscus in the tube. A radiation source is placed facing the periphery of the tube and a photoelectric device faces the periphery of the same part of the tube but is angularly offset with respect to the light from the source incident on the tube, and receives light reflected from the internal surface of the tube when no liquid is present.

Ultrasonic transducers are known to be useful in detecting the level of liquid contained in vessels or vats.

Finally, ultrasonic emitters and detectors have been used to measure liquid viscosity, the presence and orientation of particles in a mixture and certain other properties of fluids and mixtures. The known techniques using ultrasound employ methods and apparatus for measuring the attenuation of an ultrasonic wave and correlating such attenuation with the fluid property to be determined. Exemplary of such applications and U.S. Pat. Nos. 3,194,057; 2,966,056; and 2,755,662.

All of the aforesaid techniques and devices have disadvantages regarding accuracy, reproducibility, convenience and/or economies which are overcome by the method and apparatus of the present invention.

SUMMARY OF THE INVENTION

Apparatus and method are provided for automatically measuring the viscosity of a liquid comprising a viscometer tube having an inlet and an outlet and a time-interval measuring zone, at least two sets of ultrasonic transducers, one sending transducer and one receiving transducer per set, mounted so as to transmit sound waves through the time-interval measuring zone and any liquid contained therein, one transducer set being mounted at a desired distance downstream in the flow path from the other transducer set, thereby to sense the passage or absence of liquid through the measuring zone as a result of the variation in sound absorption by the liquid and air, sonic timing means connected to the transducers to measure the time interval between the time a liquid meniscus in the tube passes one set of transducers and the time the meniscus passes the second set of transducers, and sequence control means for automatically directing the flow of the liquid into and through the viscometer and energizing the sonic timing means.

Preferably, computer means are provided for computing viscosity of the liquid from the measured time-interval and the additional system flow parameters.

The viscometer tube is preferably of the Ubbelohde type modified so that the cross-section of the time-interval measuring zone is substantially rectangular in shape.

BRIEF DESCRIPTION OF THE DRAWINGS

In the drawings:

FIG. 2 is a side elevation of the viscometer apparatus of this invention with a portion broken away;

FIG. 3 is a top plan view of the viscometer apparatus;

FIG. 4 is a fragmental front elevation with a portion broken away; and

FIG. 5 is an enlarged top plan view of the viscometer apparatus, in part in cross-section, taken along the line 5—5 of FIG. 4.

DETAILED DESCRIPTION OF THE PREFERRED EMBODIMENTS WITH REFERENCE TO THE DRAWINGS

Figure 1:
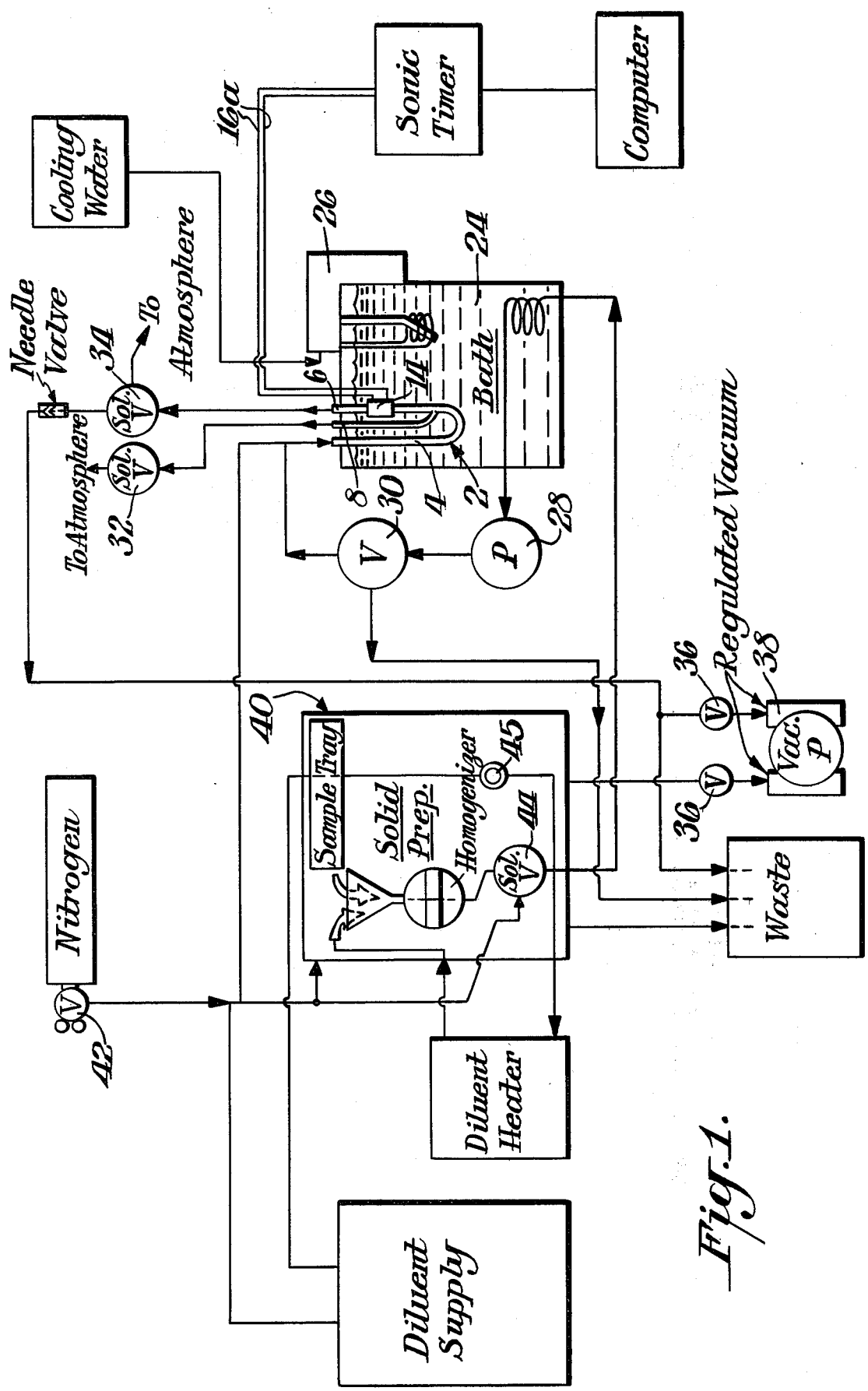
FIG. 1 is a schematic diagram of the viscometer of this invention and accessories.

Apparatus and method are provided to automatically measure the viscosity of a solution. The apparatus employs at least two sets of piezo electric ultrasonic accoustical transducers mounted along the length of a modified viscosity tube. As the meniscus of the liquid being measured passes the first transducer, a timer is actuated. As the meniscus passes the second transducer, the timer is stopped. The measured time interval enables calculation of the solution viscosity. The invention provides highly improved accuracy and descreased test time for solution viscosity measurements, while eliminating the variables encountered in conventional optical or thermistor measurements resulting from the opacity or thermal conductivity of the liquid measured.

The piezo electric ultrasonic accoustical transducers employed with this invention preferably oscillate in the (1) MH$_z$ range. They may be used in conjunction with most standard viscosity tubes. Preferably the viscosity tube is modified to conform with the cross-sectional requirements necessary to obtain good wet-to-dry signal ratio. This may be accomplished by using precision 3×9 mm. I.D. glass tubing having high dimensional qualities and low striation. Preferably, a 6 cm. length of this rectangular glass tubing is used to replace the conventional circular tube section above the precision capillary tube in the viscometer.

The two sets of transducers can be mounted in an epoxy block, and a 3×5×2.5 cm. epoxy block is satisfactory. A groove or inset is formed in the block along its length to accomodate the rectangular glass tube measuring section. The block containing the transducers is held in place on the rectangular glass tube section by a spring clip to be discussed in more detail below.

In operation with the vertical glass measuring tube having the transducer block attached thereto, one transducer set is mounted in the block near the top of the block, one transducer being located on either side of the inset, and is used to initiate the timing sequence. The other transducer set is mounted near the bottom of the epoxy block, one transducer being located on either side of the inset, and this set signals the end of the timing sequence. The transducers are oriented in a plane perpendicular to the centerline of the capillary tube in the viscometer and the rectangular glass tube section. Such orientation optimizes the meniscus sensing capabilities of the system and provides a timing accuracy of up to plus or minus one millisecond, and the reflux time is reproducible to the same degree.

Preferred accessories to the viscometer include a thermostatable sampling turntable or a solid sample processor and a pump and valving system for the infusion and withdrawal of samples. Solenoid valves control regulated vacuum for charging the viscometer. A sensitive temperature monitoring system may be used to provide either a go- no go signal or a means for determining the viscosity on a temperature-related basis. The computational operations of the system, including data processing and resultant data print-out, can be accomplished using a microcomputer such as the Hewlett-Packard HP-85.

A detailed description of the invention and its accessories is best provided by reference to the accompanying drawings.

FIG. 1 shows a schematic diagram of the viscometer of this invention and accessories. For purposes of illustration and in a preferred embodiment, a modified Ubbelohde micro viscometer 2 is immersed in a constant-temperature bath 24, the bath temperature being controlled by temperature regulator 26. The viscometer 2 has sample inlet tube 4, measuring tube 6 to which transducer block 14 is attached, and vent tube 8.

To make a viscosity measurement of, say, a solution of polyethylene terephthalate (PET) in an appropriate diluent, the solid PET sample and diluent are prepared in the solid preparation unit 40. Diluent is introduced to the homogenizer by means of the diluent pump 45 adjustable by its stroke length. The solid sample and diluent are vigorously mixed until the sample is completely dissolved and then the solution sample is automatically fed to the viscometer by automatic actuation of solenoid valve 44, pump 28 and valve 30. The solution sample is charged in the viscometer by means of the regulated vacuum shown and valves 36, solenoid valve 34 is open and solenoid valve 32 is closed. Once sufficient sample is drawn into the measuring zone and prior to the viscosity measurement, valve 34 is closed and valve 32 is opened, thereby opening vent 8 and measuring tube 6 to the atmosphere and permitting the solution sample to flow downward through measuring tube 6 and the precision capillary tube therein. As the solution meniscus passes each set of transducers located in the block 14 on measuring tube 6, the sound absorption to the receiving transducer is distinctly altered. These changes in absorption signal are sensed by the sonic timer shown through signal leads 16a and the precise time interval between the instant solution meniscus passes the upper transducers and the instant the meniscus passes the lower transducers is measured and preferably is sent to the computer for automatic processing by known techniques.

At the end of each viscosity measurement, the valves are reversed and the remaining solution is sent to waste by means of nitrogen pressure and valve 42 shown in FIG. 1. The system is flushed with excess subsequent sample material to cleanse it prior to analysis.

By this method, extremely precise viscosity data are obtained in an unexpectedly short testing time providing a significantly larger number of tests in a given time.

FIG. 2 shows the modified Ubbelohde tube 2 used in this illustration of the invention in side elevation. Therein, solution sample is introduced through inlet tube 4, accummulating in the reservoirs shown and passing upwardly through precision capillary tube section 10 and upward through measuring section 12 in measuring tube 6. The measuring section 12 is modified to have a substantially rectangular cross section as seen in FIG. 5 to provide an improved signal from the transducers. The transducers are mounted in block 14 which is attached to the measuring tube by means of a spring-loaded clamp 18 having "o"-ring 20. Spring claim 18 is rotatable as indicated by the arrow shown to permit easy attachment and removal of transducer block 14 to and from measuring section 12. Transducer lead wires 16 are shown for completeness. The precision capillary tube 10 is shown broken away.

FIG. 3 is a top plan view of the viscometer having sample inlet tube 4, measuring tube 6 having measuring section 12, and vent tube 8. Rotatable spring clamp 18 having "o"-ring 20 secures the transducer block 14 to measuring section 12. Clamp 18 is shown in phantom rotated 180° to enable removal of block 14 therefrom.

FIG. 4 shows a front elevation of the viscometer wherein transducer block 14 is attached to measuring section 12 of tube 6 by means of spring loaded clamp 18 and "o"-ring 20. The transducers 22 are shown in phantom. For completeness, tubes 4 and 8 are shown and precision capillary tube 10 is shown broken away.

FIG. 5 is an enlarged top plan view of the viscometer of this invention taken along line 5—5 of FIG. 4. Transducer block 14 having transducers 22 embedded therein is attached to measuring section 12 by means of spring clamp 18. The preferred cross-section of the measuring section 12 is as shown. The relative positions of inlet tube 4, vent tube 8, capillary tube 10 and transducer lead wires are all shown for completeness.

While the invention has been disclosed herein in connection with certain embodiments and detailed descriptions, it will be clear to one skilled in the art that modifications or variations of such details can be made without deviating from the gist of this invention, and such modifications or variations are considered to be within the scope of the claims hereinbelow.

I claim:

1. Apparatus for automatically measuring the viscosity of a liquid comprising:
   (a) a viscometer tube having an inlet and an outlet and a time-interval measuring zone,
   (b) at least two sets of ultrasonic transducers, one sending transducer and one receiving transducer per set, mounted so as to transmit sound waves through said time-interval measuring zone and any liquid contained therein, one transducer set being mounted at a desired distance downstream in the flow path from the other transducer set, thereby to sense the passage or absence of liquid said measuring zone as a result of the variation in sound absorption by said liquid and air,
   (c) sonic timing means connected to said transducers to measure the time-interval between the time a liquid meniscus in said tube passes one set of transducers and the time said meniscus passes the second set of transducers, and
   (d) sequence control means for automatically directing the flow of said liquid into and through said viscometer and energizing said sonic timing means.

2. The apparatus of claim 1 including computer means for computing viscosity of said liquid from said measured time-interval and the additional system flow parameters.

3. The apparatus of claim 1 wherein said viscometer tube is one of the Ubbelohde type.

4. The apparatus of claim 3 wherein said Ubbelohde tube is modified to provide a time-interval measuring zone which is substantially rectangular in flow cross-section.

5. The method for automatically measuring the viscosity of a liquid comprising measuring the time-interval of passage of the meniscus of said liquid as it descends through an otherwise conventional viscometer tube utilizing a sonic timer and at least two sets of ultrasonic transducers, one sending transducer and one receiving transducer per set, mounted so as to transmit sound waves through said liquid, one transducer set being mounted at a desired distance downstream in the flow path from the other transducer set, thereby sensing the passage of liquid through said tube as a result of the variation in sound absorption by liquid and air.

* * * * *